United States Patent
Gow

Patent Number: 5,299,937
Date of Patent: Apr. 5, 1994

[54] DENTAL INSTRUMENTS HAVING DIAMOND-LIKE WORKING SURFACE

[75] Inventor: Robert H. Gow, Houston, Tex.

[73] Assignee: SI Diamond Technology, Inc., Houston, Tex.

[21] Appl. No.: 921,529

[22] Filed: Jul. 29, 1992

[51] Int. Cl.⁵ .............................................. A61C 3/06
[52] U.S. Cl. ..................................... 433/165; 433/166
[58] Field of Search ............... 433/165, 166, 125, 142, 433/147, 144, 102

[56] References Cited

U.S. PATENT DOCUMENTS

| | | | |
|---|---|---|---|
| 4,190,958 | 3/1980 | Martin et al. | |
| 4,466,795 | 8/1984 | Plischka | |
| 4,681,541 | 7/1987 | Snaper | 433/165 |
| 4,684,346 | 8/1987 | Martin | 433/166 |
| 4,708,653 | 11/1987 | Eichen et al. | 433/165 |
| 4,731,019 | 3/1988 | Martin | 433/166 X |
| 4,895,146 | 1/1990 | Draenert | |
| 4,987,007 | 1/1991 | Wagal et al. | 118/723 X |
| 5,035,618 | 7/1991 | Katz et al. | 433/165 X |
| 5,098,737 | 3/1992 | Collins et al. | 427/249 X |

OTHER PUBLICATIONS

Lexis search report.
Schmidt Instruments, Inc. brochure "Amorphic Diamond ™ Coatings".

*Primary Examiner*—Gene Mancene
*Assistant Examiner*—Nicholas D. Lucchesi
*Attorney, Agent, or Firm*—Pravel, Hewitt, Kimball & Krieger

[57] ABSTRACT

Disclosed are dental instruments having a working surface comprising a diamond-like coating. The coating may be applied by the laser ablation process. Also disclosed is a method of operating on teeth or dental workpieces by contacting the teeth or workpieces with a diamond-like coating.

20 Claims, 1 Drawing Sheet

DENTAL INSTRUMENTS HAVING DIAMOND-LIKE WORKING SURFACE

BACKGROUND OF THE INVENTION

1. Field of the Invention

The present invention relates to dental instruments and to a method of operating on teeth or dental workpieces. In another aspect, the present invention relates to improved dental instruments for teeth or dental workpieces having a contact surface comprising a coating of dehydrogenated diamond-like film having both amorphous and microcrystalline atomic structures and to a method of operating on teeth or dental workpieces utilizing such improved instruments.

2. Description of the Related Art

Many different types of dental instruments are utilized in the practice of dental medicine. For example, dental burs are used to drill into teeth, and to shape internal and external tooth surfaces. Endodontic drill files are utilized in root canal dentistry to clean out the root canal. Scaler dental instruments are utilized for treating periodontal disease. Dental workpieces, such as inlays, onlays, crowns and bridges are operated upon utilizing cutting discs or dental burs. Models of patients' mouths are operated upon, requiring cutting of stone or plaster.

It is important that these dental instruments be sharp and hard to operate properly upon teeth, dental workpieces and models.

Generally, dental instruments are operated at very high speeds, generally in excess of 100,000 rpm, and particular care is taken with lubrication and cooling. However, in spite of advancements in dental instruments and dental procedures, the patient will still be traumatized to a certain extent.

Improvements in the durability of dental instruments would increase patient comfort, because a dental instrument that remains sharp longer will generally in the long run be less traumatic. To the dentist, a more durable dental instrument would lessen the need to change the instrument during a procedure because of dulling of the instrument.

As a consequence of sharper instruments, drilling and grinding speeds can be shortened, vibration effects from a non-uniformly worn dental instrument can be reduced, and to these improvements can additionally be added improved lubricity and heat transfer properties. Unfortunately, inherent in conventional efforts to make a sharp and durable dental instrument is that these materials tend to be brittle, and crack and break. Breakage during a dental procedure represents danger to the patient. A piece of the instrument may come loose and not be readily retrievable, or may jam in a tooth crevice, requiring sacrificing some of the tooth. These tendencies may be countered not only by maintaining sharpness longer, but also by providing toughness as well.

Not surprisingly, there have been many attempts in the prior art to improve the durability of dental instruments.

U.S. Pat. No. 4,190,958, issued Mar. 4, 1980 to Martin et al., discloses an endodontic drill file having a drilling surface coated with diamond particles.

U.S. Pat. No. 4,466,795, issued Aug. 21, 1984, to Plischka, discloses a helocoidally grooved dental bur having a working surface covered with diamond particles.

U.S. Pat. No. 4,681,541, issued Jul. 21, 1987 to Snaper, discloses a dental bur having a metal nitride or carbide layer applied over diamond particles.

U.S Pat. No. 4,731,019, issued Mar. 15, 1988 to Martin, discloses a scaler dental instrument that is coated with diamond particles.

U.S Pat. No. 4,895,146, issued Jan. 23, 1990 to Draenert, discloses a surgical bone grinding instrument having a coating of diamond particles in size of about 30 to about 250 microns.

While the use of a coating of diamond particles on the contact or working surface of a dental instrument represents an improvement over conventional dental instruments, such coatings still need improvement. These diamond particles are generally embedded into a relatively soft substrate. As the substrate erodes, the diamond crystals are lost. While a coating such as at disclosed in the '541 Snaper patent will lengthen the life of such coatings of diamond particles, the particles are still susceptible to being dislodged.

In addition, during dental operations, there is a build up of ground material in the grooves of dental burs, disks, drills and bits. This build up reduces function until the bit must be discarded for a new one since it is presently not practical to clean out these grooves.

Therefore, the need exists in the dental instrument art for a dental instrument with a contact surface with improved durability. There also exists a need in the dental instrument art for a dental instrument that can be more easily cleaned of the build-up of ground material.

SUMMARY OF THE INVENTION

According to one embodiment of the present invention there is provided an improved dental instrument wherein the improvement comprises a tooth or dental workpiece contact surface comprising coating of dehydrogenated diamond-like film having both amorphous and microcrystalline atomic structures. This dental instrument having a coating is more durable that prior art instruments utilizing diamond particles. In addition, build up of ground material is easily removed by brushing.

According to another embodiment of the present invention there is provided an improved method of operating on a tooth or dental workpiece wherein the improvement comprises operating on the tooth or dental workpiece with a surface comprising a coating of dehydrogenated diamond-like film having both amorphous and microcrystalline atomic structures.

DETAILED DESCRIPTION OF THE INVENTION

Figure 1A:
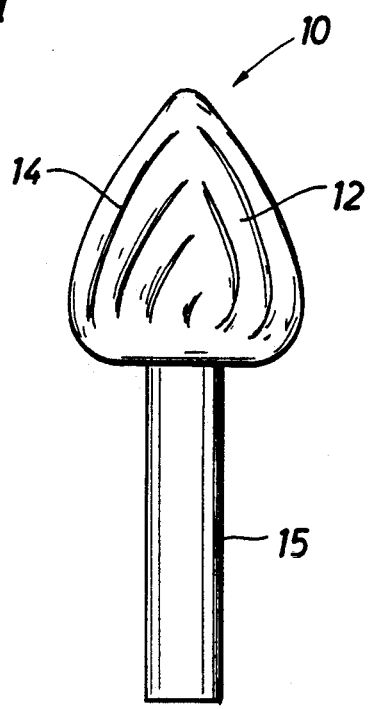

The dental instruments of the present invention may generally be any that are utilized in the practice of dental medicine, except of course that these instruments are improved by a working surface that comprises diamond-like coating. Such instruments include dental burs, drills, disks, and bits. Such a diamond-like coating may be applied over other prior art coatings or may be applied directly to the instrument substrate.

For example, the endodontic drill of U.S. Pat. No. 4,190,958, the helocoidally grooved dental bur of U.S. Pat. No. 4,466,795, the dental bur of U.S. Pat. No. 4,681,541, the scaler instrument of U.S. Pat. No. 4,731,019, and the surgical bone grinding instrument of U.S. Pat. No. 4,895,146, all herein incorporated by reference, could all be improved by applying a coating according to this invention, either directly to the substrate or over the diamond particle or metal coatings of these instruments.

The dental instruments of the present invention may be utilized in operating on teeth and dental workpieces such as inlays, onlays, crowns, bridges and parts thereof and on models of patients' mouths.

In the present invention, the coating will be utilized on the contact or working surface, i.e., the surface that comes into contact with and operates upon the tooth or dental workpiece.

DIAMOND-LIKE COATING

The amorphic or diamond-like coating of the present invention may be applied by any suitable method that will produce the desired coating. The coating is generally composed of densely packed nodules of sp$^3$ bonded carbon linked by a matrix of mixed carbon polytypes. Suitable apparatus and methods of applying such a coating include laser ablation as disclosed in U.S. Pat. Nos. 4,987,007, issued Jan. 22, 1991 to Wagal et al. and 5,098,737, issued Mar. 24, 1992 to Collins et al, both herein incorporated by reference.

The coating utilized in the dental instruments of the present invention must generally be thick enough to withstand the rigors of the dental procedure in which it will be utilized. Generally, the coating thickness will generally be at least about 200 Angstroms. Preferably, the coating thickness is in the range of about 2,000 Angstroms to about 30,000 Angstroms, and most preferably, in the range of about 5,000 Angstroms to about 15,000 Angstroms.

The coating of dehydrogenated diamond-like film having both amorphous and microcrystalline atomic structures utilized in the dental instruments of the present invention will generally have less that 5 percent hydrogen impurities. Preferably, the hydrogen impurities will be less than about 2 percent, and most preferably less than about 0.5 percent.

EXAMPLE 1

A dental instrument consisting of a bur is used by dental laboratories in bulk trimming operations. The material to be trimmed is typically a green plaster or "stone" used for forming models of the human mouth. The models must be shaped with precision. During cutting of the stone to remove excess from the model, a considerable amount of solid must be removed. Prior cutting means include the use of titanium nitride burs. The burs typically contain small grooves to provide cutting surfaces. The burs become dull and the grooves quickly become plugged or filled with the drilled solids.

FIG. 1(a) shows such a bur 10 having a contact surface 12 with grooves 14 coated with amorphic diamond material produced by laser ablation deposition. In the embodiment shown, shaft 15 of bur 10 was not coated, although it may optionally be coated. The amorphous diamond material utilized as contact surface 10 is described in U.S. Pat. Nos. 4,987,007 and 5,098,737. The laser used to produce the coated dental instruments had a power greater than 10$^9$ watts per square centimeter. It was a Nd-Yag, Q-switched laser which produced an instantaneous power per pulse of at least several hundred millijoules. The target was high purity graphite in the form of a cylindrical rod. There was no charged electrode in the vacuum chamber during the deposition of diamond.

Bur 10 coated with diamond-like material to a thickness of about 2000 to 3000 angstroms did not become dull after use for 2 to 3 times as long as the prior uncoated burs. Surprisingly, it was found that the grooves did not fill quickly with solid material, and the material which filled the grooves could be very easily brushed from the grooves. This improvement is believed to be the result of the low frictional resistance and low adhesional energy of the diamond-coated surface. The combined effects of wear resistance and low adhesion of cutting particles provided a much more effective bur.

EXAMPLE 2

Figure 1B:
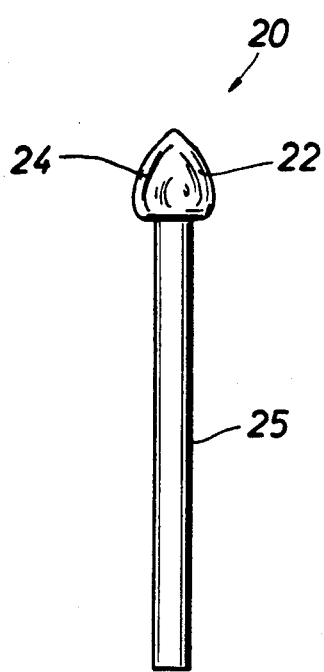

FIG. 1(b) illustrates margin trimming bur 20 having contact surface 22 and grooves 24 comprising a diamond-like material as described in Example 1. As with bur 10 in Example 1, shaft 25 of bur 20 is not coated but optionally be coated. Bur 20 is used in shaping or contouring the very critical part of a model of a tooth that is being used to prepare a crown.

The diamond-coated margin trimming bur 20 was used to cut more than 800 dies, after which it was still cutting very efficiently. An uncoated bur of identical shape would cut only about 500 dies.

EXAMPLE 3

Figure 1C:
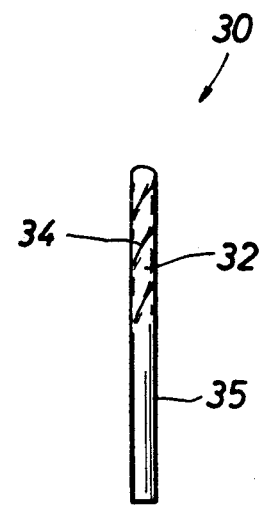

FIG. 1(c) shows a small bit 30 which is used in trimming the critical area of models used to prepare crowns, and has a contact or working surface 32 and grooves 34 and comprises a diamond-like coating as described in Example 1. Shaft 35 is uncoated in the embodiment shown, but may optionally be coated. Bit 30 was made of tungsten carbide. The diamond coating increased the life of the bit and prevented rapid plugging of the grooves. Unlike grooves in uncoated bits, grooves of bit 30 which plugged were very easily cleaned by brushing.

I claim

1. An improved dental cutting instrument wherein the improvement comprises a tooth or dental workpiece contact surface, the contact surface having a plurality of grooves formed therein, comprising said surface further a coating of dehydrogenated diamond-like film having both amorphous and microcrystalline atomic structures.

2. The instrument of claim 1 wherein the contact surface has a thickness in the range of at least about 200 Angstroms.

3. The instrument of claim 1 wherein the contact surface is applied utilizing laser ablation.

4. The instrument of claim 1 wherein the instrument is selected from the group consisting of dental burs, drills, disks and bits.

5. The instrument of claim 1 wherein the contact surface has a thickness in the range of about 2,000 Angstroms to about 30,000 angstroms.

6. The instrument of claim 1 wherein the contact surface has a thickness in the range of about 5,000 Angstroms to about 15,000 Angstroms.

7. The instrument of claim 1 wherein the contact surface is applied directly to the instrument.

8. The instrument of claim 1 wherein the contact surface is applied over one or more diamond particle or metal coatings.

9. The instrument of claim 1 wherein the surface coating comprises less than about 5 percent hydrogen impurities.

10. The instrument of claim 1 wherein the contact surface is applied by laser ablation, comprises less than about 0.5 percent hydrogen impurities and has a thickness in the range of about 2,000 angstroms to about 30,000 angstroms, and wherein the instrument is selected from the group consisting of dental burs, drills, disks and bits.

11. An improved method of operating on a tooth or dental workpiece wherein the improvement comprises operating on the tooth or dental workpiece with a cutting surface, the surface having a plurality of grooves formed therein, said surface further comprising a coating of dehydrogenated diamond-like film having both amorphous and microcrystalline atomic structures.

12. The method of claim 11 wherein the contact surface has a thickness in the range of at least about 200 Angstroms.

13. The method of claim 11 wherein the contact surface is applied utilizing laser ablation.

14. The method of claim 11 wherein the instrument is selected from the group consisting of dental burs, drills, disks and bits.

15. The method of claim 11 wherein the contact surface has a thickness in the range of about 2,000 Angstroms to about 30,000 angstroms.

16. The method of claim 11 wherein the contact surface has a thickness in the range of about 5,000 Angstroms to about 15,000 Angstroms.

17. The method of claim 11 wherein the contact surface is applied directly to the instrument.

18. The method of claim 11 wherein the contact surface is applied over one or more diamond particle or metal coatings.

19. The method of claim 11 wherein the surface coating comprises less than about 5 percent hydrogen impurities.

20. The method of claim 11 wherein the contact surface is applied by laser ablation, comprises less than about 0.5 percent hydrogen impurities and has a thickness in the range of about 2,000 angstroms to about 30,000 angstroms, and wherein the instrument is selected from the group consisting of dental burs, drills, disks and bits.

* * * * *